United States Patent [19]

Romette et al.

[11] Patent Number: 4,957,706
[45] Date of Patent: Sep. 18, 1990

[54] DEVICE FOR PRESERVING STERILITY DURING SAMPLING FROM CULTURE MEDIUM CONTAINERS

[75] Inventors: Jean-Louis Romette, Orrouy; Joël G. Fourreau, Compiegne, both of France

[73] Assignee: Centre National de la Recherche Scientifique, Paris, France

[21] Appl. No.: 52,409

[22] Filed: May 21, 1987

[30] Foreign Application Priority Data

May 22, 1986 [FR] France .................... 86 07329

[51] Int. Cl.$^5$ .................... G01N 1/10
[52] U.S. Cl. .................... 422/100; 422/81;
422/102; 422/103; 422/104; 436/54; 436/180;
137/625.12; 137/625.65; 137/625.67;
137/625.26; 251/92; 251/325; 73/863.73;
73/863.83; 73/864.18; 73/864.63
[58] Field of Search .............. 422/81, 100, 103, 63,
422/102, 104; 436/54, 180; 137/625.11, 625.12,
625.65, 625.67, 625.26, 625.27, 254; 73/863.31,
863.73, 863.83, 864.16–864.18, 864.21, 864.61,
864.63; 251/92, 325

[56] References Cited

U.S. PATENT DOCUMENTS 4,585,623  4/1986  Chandler .................. 422/100 X
4,640,821  2/1987  Mody et al. ............... 422/81
4,649,028  3/1987  Kaltenbach et al. ........ 422/103 X Primary Examiner—Robert J. Warden
Assistant Examiner—Lynn M. Kummert
Attorney, Agent, or Firm—Burns, Doane, Swecker & Mathis

[57] ABSTRACT

A device for preserving sterility during the taking of samples for analysis from culture medium containers. This device comprises a holder containing a sampling chamber which encloses a sliding piston fitted at one end with a toric cavity for removal of the sample for analysis, and a dilution chamber linked to the first chamber by a duct. The second chamber is divided into two parts by a central bearing and contains two sliding pistons which may abut respectively the opposite sides of the bearing. The second chamber comprises an inlet for the dilution solvent.

15 Claims, 9 Drawing Sheets

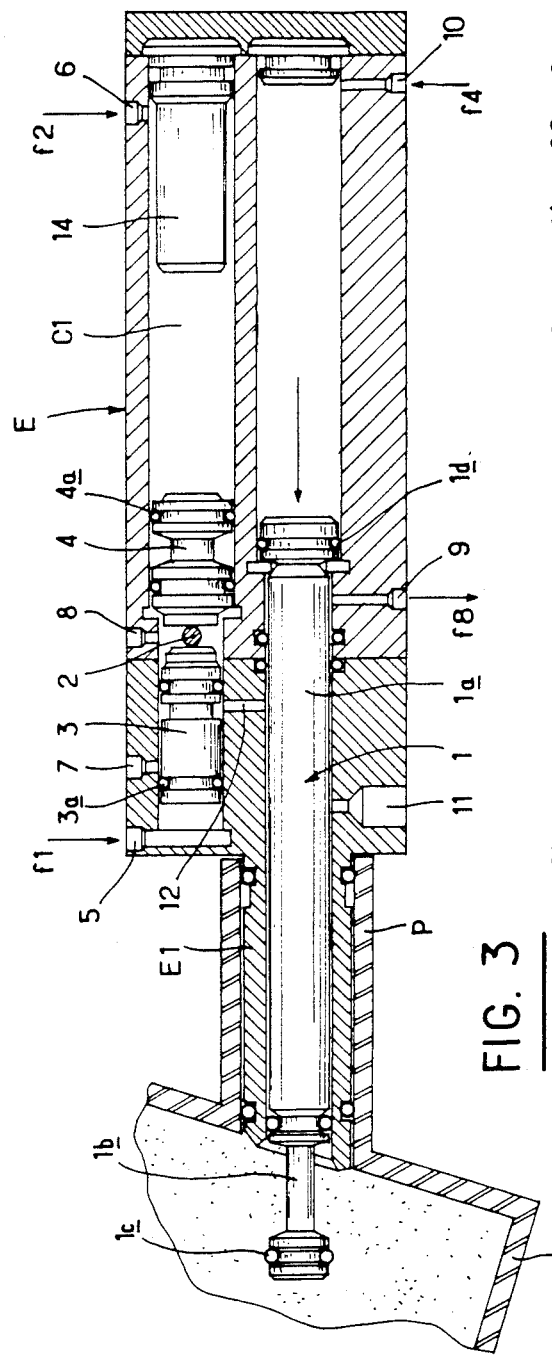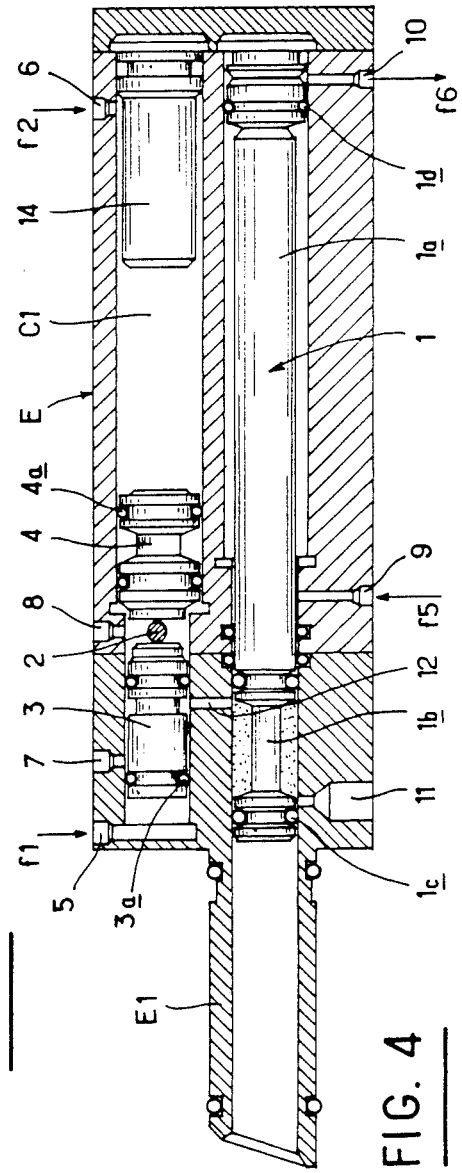
FIG. 3
FIG. 4

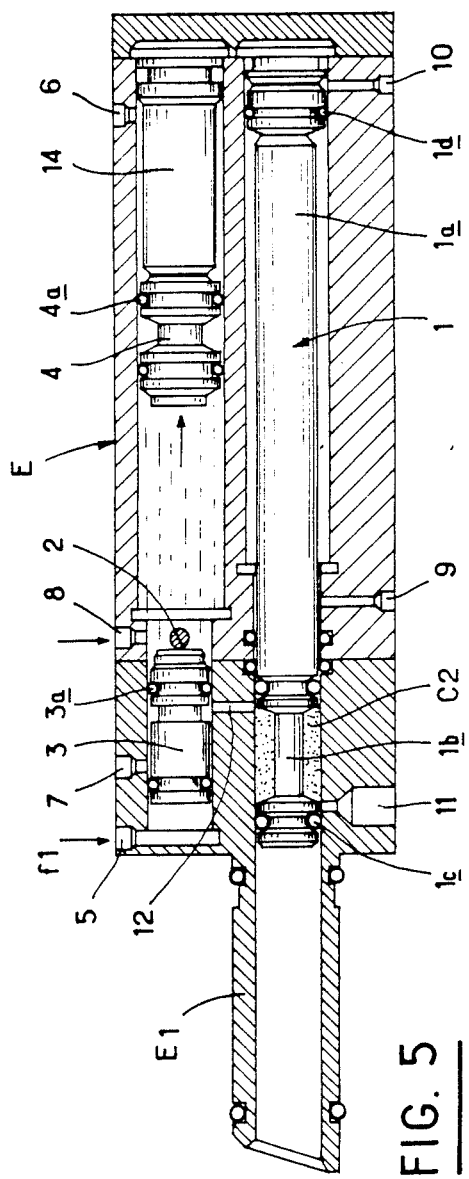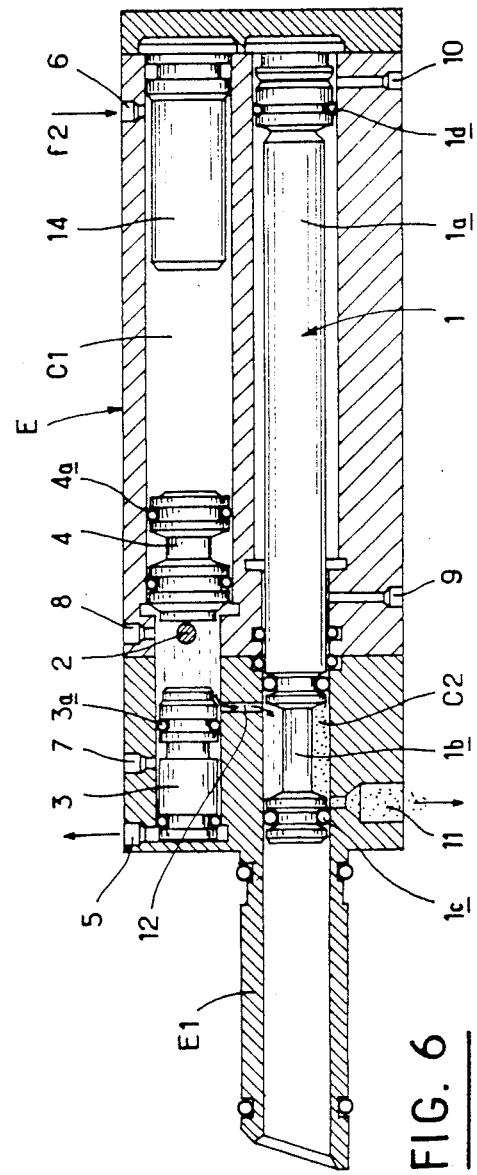

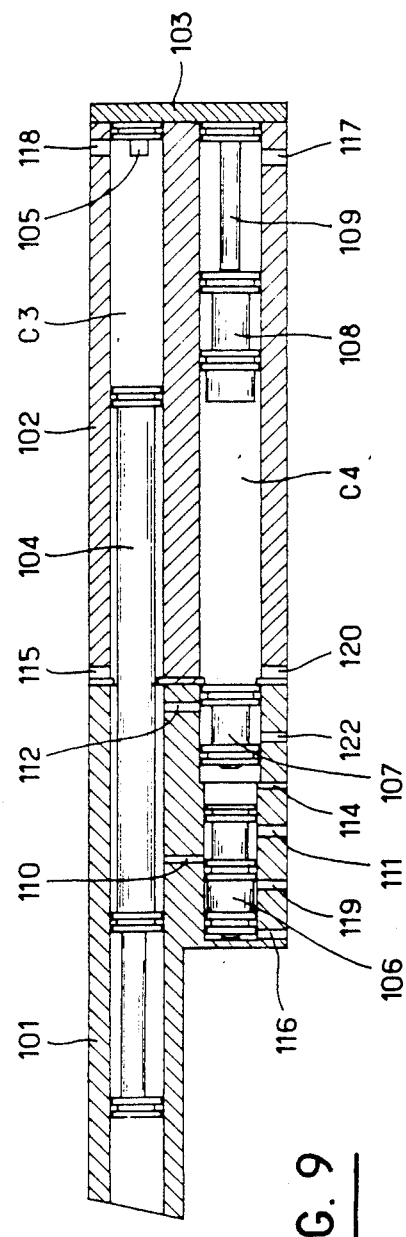
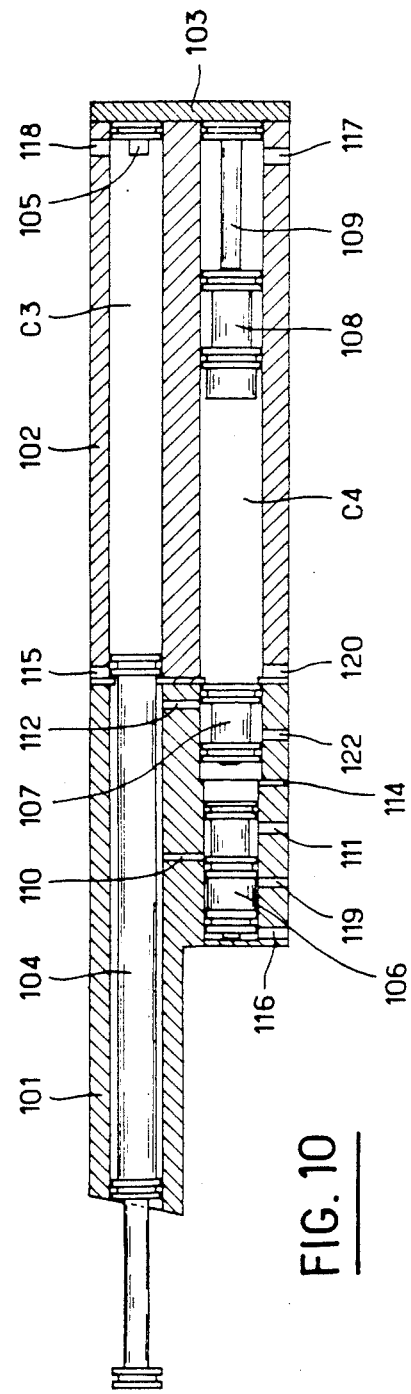
FIG. 9
FIG. 10

DEVICE FOR PRESERVING STERILITY DURING SAMPLING FROM CULTURE MEDIUM CONTAINERS

FIELD OF THE INVENTION

The present invention relates to the taking of samples from sterile containers. The invention uses in particular a device for preserving sterility during the taking of samples for analysis from culture medium containers.

BACKGROUND OF THE INVENTION

Until now, devices of the prior art, most of which functioned manually, did not allow sampling without the risk of contaminating the culture medium. Inconvenience was inherent, since samples were obtained manually with poor control of volume precision and it was not possible to exclude the risk of contamination by the external environment. Nevertheless, one of the greatest risks associated with devices of the prior art was contamination of the fermentation container.

BRIEF DESCRIPTION OF THE INVENTION

One of the aims of the present invention is to provide a sampling device for reproducible removal of samples of known volume.

The invention also provides a sampling device for repeated sampling of known volumes, while avoiding contamination of the culture medium from which the said samples are taken.

The invention also relates to the development of a sampling device that minimizes risks of contamination of the fermentation medium through easy sterilization of component parts involved in removal of fixed-volume samples, while allowing automatic dilution of the samples in solvent, cooling of the moving parts of the device and the drying of the said moving parts with a sterile liquid.

DETAILED DESCRIPTION OF THE EMBODIMENTS

The present invention, therefore, relates to a device for preserving sterility during the taking of samples for analysis from culture medium containers. This device comprises a holder containing a so-called sampling chamber which encloses a sliding piston fitted at one end with the means for removal of the sample for analysis, and which is extended by a nozzle which provides a watertight fit in the inlet port provided in the culture medium container. The second, so-called dilution chamber is linked to the first chamber by a duct and is divided into two parts by a bearing means and contains at least two sliding pistons which may abut respectively the opposite sides of the bearing. The first chamber comprises at least one sample outlet, and the second chamber comprises at least one solvent inlet.

The sampling device according to the present invention also presents the following special characteristics:

chamber-piston contact is watertight;

the piston in the first chamber has a shoulder in the part opposite to the sampling part;

the second chamber comprises a stop the size of which is chosen so as to determine the dilution volume, which is limited by the faces opposite the pistons and the internal faces of the said chamber;

the stop is mobile and is actuated by external means, for example a computer-controled stepping motor for adjustment of the dilution volume, and hence of the sample dilution factor;

various pistons are actuated by motor means, for example, of hydraulic, pneumatic or magnetic type. In the case of pneumatic control of the pistons, it is advantageous to use a compressed air supply, with several feed valves operated mechanically, for example by automated cams, or electronically, for example by a microprocessor.

According to another variant of the embodiment of the sampling device according to the present invention, the device comprises two bodies joined, for example, by screwing, defining a first cylindrical, so-called sampling chamber and a second cylindrical, so-called dilution chamber, which contain respectively one and three sliding pistons. This variant of the embodiment can be used to advantage if the sampling chamber is placed above the dilution chamber.

These modifications improve sterility of the sampling piston when it penetrates the fermentation vessel, guarantee efficacious sterilization, ensure separation of sterilization condensates and sampled liquid, guarantee dilution precision, decrease costs by simplifying machining of component parts and provide faster sterilization, hence reducing overall heating.

In all cases, the means are provided for introducing solvent and for purging and washing the sampling device after each sampling cycle.

Further advantages and characteristics of the invention will become apparent upon reading the following description of a nonlimiting embodiment of the sampling device, with reference to the appended figures, in which:

FIG. 3 is a view analogous to that of FIG. 1, during sampling;

FIG. 4 is a view analogous to the previous figures, during uptake of the sample into the sampling device;

FIG. 5 is a view analogous to the previous figures, during the preparation of the volume of water used in dilution;

FIG. 6 is a view analogous to the previous figures, during dilution and rinsing;

FIG. 9 is a view analogous to FIG. 1, during sampling;

FIG. 10 is a view analogous to FIG. 1, at the closing of the vapor inlet and the end of intake;

Figure 1:
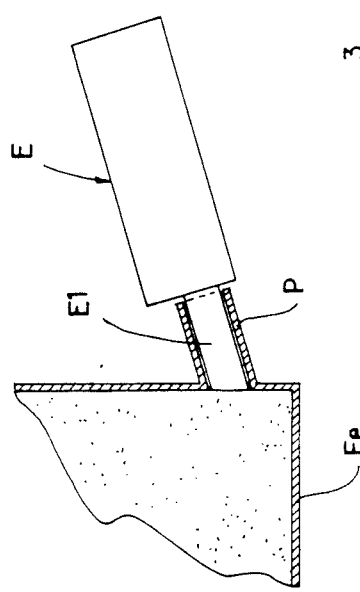
FIG. 1 is a view of an axial longitudinal section of a sampling device according to invention, fitted into an inlet port in a culture medium container of fermentation vessel.

As shown in FIG. 1, the sampling device E is inserted into an inlet port in a fermentation vessel Fe by means of a nozzle E1. The inlet port is angled upwards, with respect to the wall of the fermentation vessel, in order to return condensate to the fermentation vessel.

As shown in greater detail in FIGS. 2 to 6, the sampling device according to the present invention comprises a holder E containing an upper chamber C1 and a lower chamber C2 extended by a nozzle E1. In the lower, so-called sampling chamber C2 is a piston 1 with a shoulder 1a at the opposite end from the nozzle E1. At the other end, the piston is shaped to give a toric cavity 1b. Both sides of the toric cavity 1b are fitted with watertight toric joints 1c. Watertight toric rings are also fitted near the shoulder 1d. In the upper, or dilution, chamber C1 two pistons 3 and 4 fitted at their ends with watertight toric rings 3a, 4a are mounted on opposite sides of a central bearing 2. The dilution chamber C1 is fitted with air inlets 5, 6, as indicated by arrows f1 and f2, a vapor inlet 7 indicated by arrow f3 and a solvent inlet 8.

Figure 14:
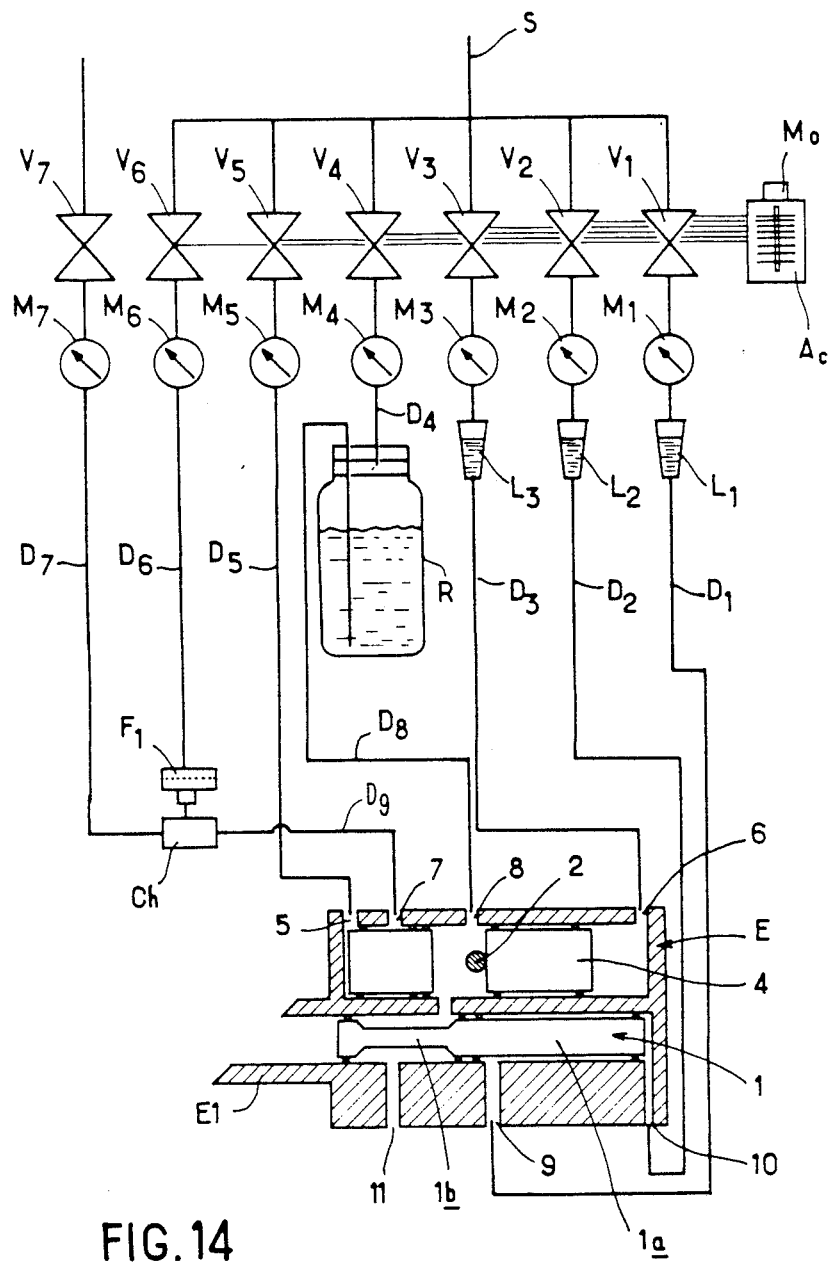
FIG. 14 is diagram of the whole sampling device according to the invention.

The sampling chamber C2 is fitted with two air inlet-outlet openings 9, 10, as indicated by arrows f3, f4, f5 and f6, respectively. Chamber C2 is also fitted with a purge opening 11, as indicated by arrow f7. Chambers 1 and 2 are connected by a duct or opening 12. In the general diagram of the sampling device according to the invention, as shown in FIG. 14, it can be seen that the sampler operates with a supply of compressed air S feeding through a series of valves V1, V2, V3, V5 the respective openings 9, 10, 6, 5 by respective ducts D1, D2, D3, D5. The compressed air is also taken in through valve V4 and duct D4 into a recipient R containing a suitable solvent, for example water, in which water under the pressure of condensed air passes through duct D8 to the solvent inlet 8. Compressed air also passes through valve V6 and duct D6 to a filter Fi where microorganisms and impurities are removed from the air which passes into the mixing chamber Ch where the purified air mixes with vapor, intake of which is controlled by valve V7 via duct D7. The compressed air/vapor mixture then passes through duct D9 to the vapor inlet 7. In a preferred embodiment, valves V1 to V7 are associated with release valves M1 to M7 and are electrically operated by an automatic cam device Ac, which is itself actuated by a reducing motor Mo. Downline from releasing valves M1, M2, M3, lubricators can be used, but this is not obligatory since the sampling device according to the invention can also operate efficaciously without lubricants.

Figure 2:
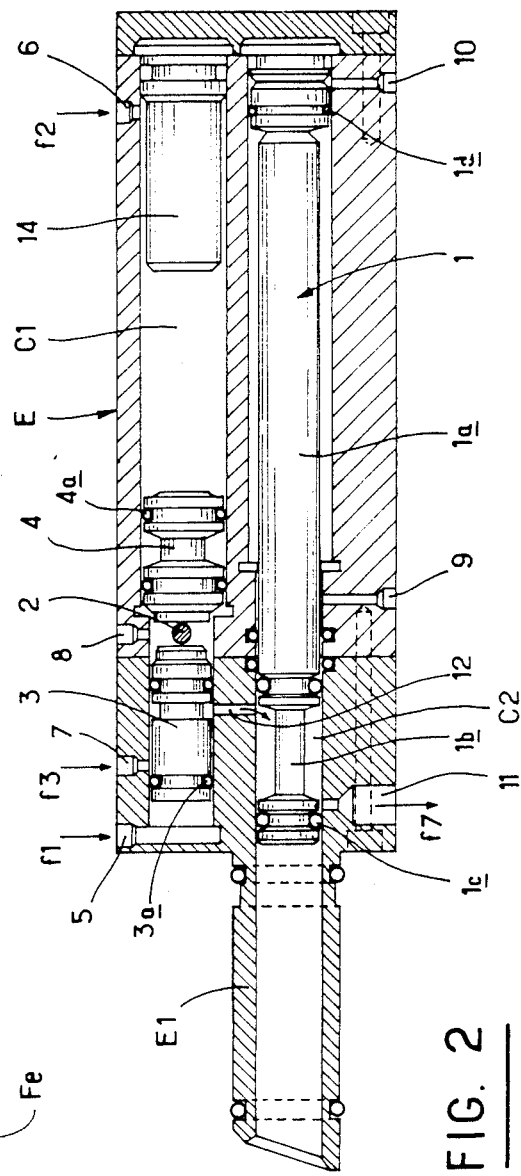
FIG. 2 is a more detailed view of an axial longitudinal section of a sampling device according to the invention, during sterilization.
Figure 7:
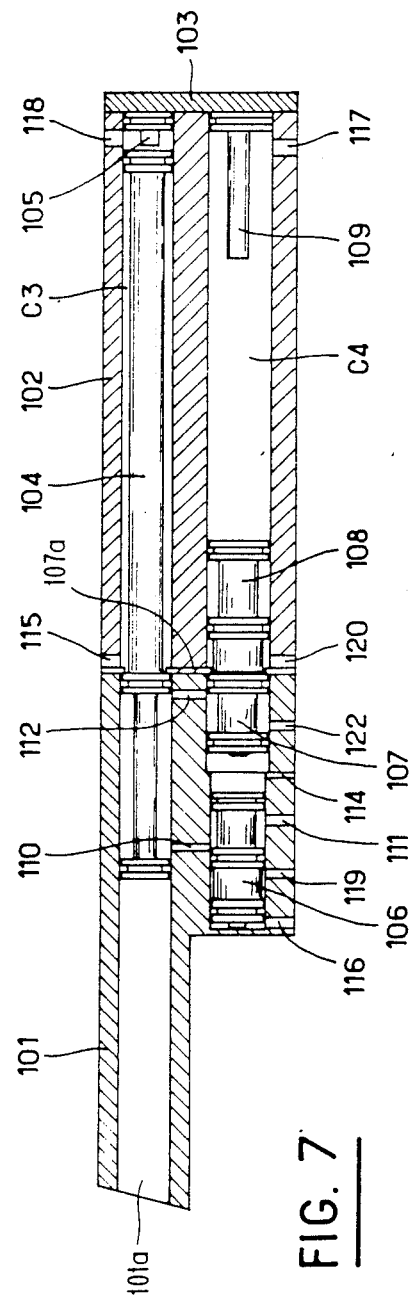
FIG. 7 is an axial longitudinal section of a variant of the embodiment of the sampling device according to the invention, during sterilization.
Figure 8:
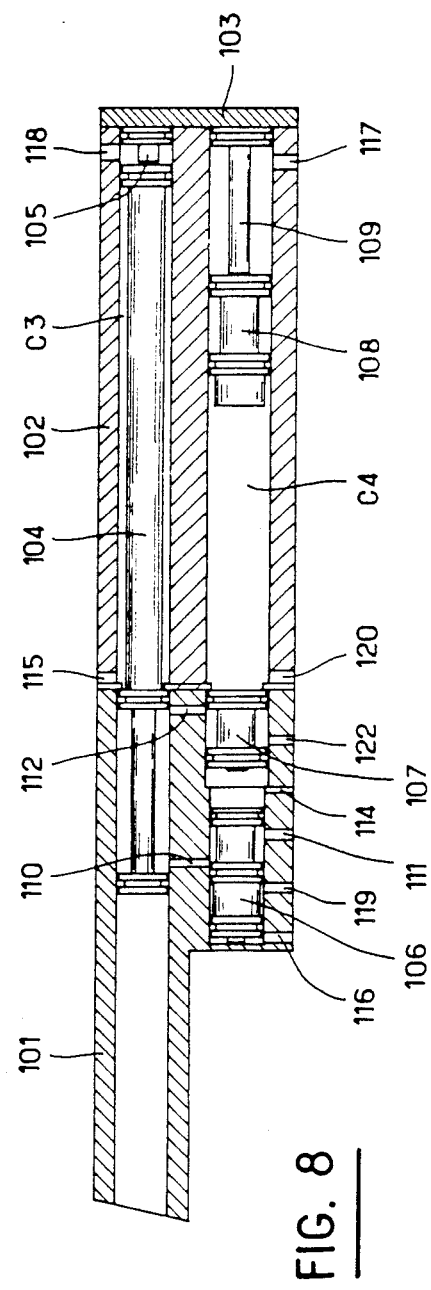
FIG. 8 is a view analogous to FIG. 1, between sterilization and sampling.

The cycle of operations for the sampling device according to the present invention is as follows:

when the sampling device E is inserted in the fermentation vessel F, as shown in FIG. 1, the operation can be defined in terms of the five major steps represented in FIGS. 2 to 6 respectively.

as shown in FIG. 2, the first step preceding use of the sampling device consists in sterilizing the components contaminated by the external environment. Valves V3, V5, V6 and V7 are open and the other valves are closed in order to bring pistons 3 and 4 into contact with bearing 2, under the effect of the air taken into chamber C1 as indicated by f1 and f2, while the filtered air mixture supplied through filter fi and the vapor are mixed in the chamber Ch before being admitted to the sampling device through inlet 8. The air purge/vapor mixture is then released through opening 11, as indicated by arrow f7.

The second step, as shown in FIG. 3, consists of obtaining of the sample. Valves V2, V4, V6 and V7 are closed and valves V3 and V5 remain open. Valve V1 is opened to insert the sampling chamber 1b of piston 1 into the fermentation vessel.

The third step, as shown in FIG. 4, consists in drawing the sample into the sampling device, by closing valve V1 and opening valve V2, while valves V3 and V5 and the other valves are closed. The air taken in as indicated by f5 through opening 9 acts on the shoulder 1a of piston 1, thus bringing the piston into contact with the wall of chamber C1. This air is released through opening 10 as indicated by f6.

The fourth step, shown in FIG. 5, consists in preparing a volume of solvent, for example water, for dilution of the sample already removed during the previous steps. All the valves of the device are closed, except for valve V4 and valve V5. The pressure of the compressed air passing through valve V5 forces piston 3 into contact with bearing 2, while the air pressure acting through valve V4, as described above, forces solvent, for example water, through inlet 8 into chamber C1. It can be seen that the faces opposite pistons 3 and 4, together with the internal faces of chamber C1, define a dilution volume which reaches a maximum when piston 4 makes contact with the stop 14 at the back wall of the chamber C1.

The fifth step, called "dilution-rinsing", consists in conveying the duly diluted sample to the analyzer, by opening of valve V3, which forces piston 4 against bearing 2, while piston 3 abuts the opposite wall of chamber C1, thus uncovering duct 12 between chambers C1 and C2 through which the solvent (dilution liquid) flows and mixes in the toric chamber 1b before flowing to the analyzer, which is not shown in the diagram, through the outlet or purge opening 11.

In the variant of the embodiment shown in FIGS. 7 to 13, the sterile sampling device according to the invention comprises two parts 101 and 102 connected by screws. Part 101 acts as a nozzle and is fixed to the fermentation vessel. At the free end of part 102 is fitted a stopper 103. Assembly of parts 101, 102, 103 defines the two cylindrical chambers, that is an upper sampling chamber C3 and a lower dilution chamber C4. In the upper chamber C3 is fitted a sampling piston 104 able to abut an end-stop 105 which renders the chamber C3 watertight. Inside chamber C4 are fitted respectively three sliding pistons, that is a so-called condensate piston 106, a so-called vapor piston 107 and a so-called diluent piston 108, the latter being able to abut an end-stop 109 intended to render chamber C4 watertight.

This variant of the embodiment of the sterile sampling device operates in the following way:

In a first operational sequence, piston 104 abuts the watertightness stop 105 on the right. Piston 106 is pushed to the left end of chamber C4, thus uncovering bores 110, 111. Piston 107 is pushed to the right of zone 101a of chamber C3 into contact with the shoulder 107a of chamber C4, thus uncovering bores 112, 120 while piston 108 abuts piston 107. These positions are obtained by the ingress of compressed air pressure through openings 114 and 115. The pressure in 114 is released and returns to atmospheric pressure before the end of sterilization to avoid leakage through a joint of chamber C3 contaminating this chamber when the vapor intake is turned off. Bores 116, 117 and 118 are at atmospheric pressure, while the electrical valves associated with bores 119 and 120 are closed. Vapor is admitted through opening 120, flows along the body of the piston 107, through bore 112 and the sampling chamber of piston 104 and is removed, like the condensates, due to the natural slope of sampling through bore 110, then along piston 106 by bore 111. After blowing, pressurization of the chamber for its temperature rise is obtained by sequencing at an electrical valve connected to bore 111. The diameters of the bores and piston bodies are designed to allow easy passage of vapor. For sterilization of the sampling chamber, the correct positioning of piston 104 is ensured by triggering of a sensor, not shown in the diagrams, which detects thrust against the watertightness stopper 105. In the second operational sequence shown in FIG. 8, before the end of sterilization, the water chamber is filled from the sampling chamber C3 by intake through bore 112, while bore 117 has been under atmospheric pressure since the operational sequence shown in FIG. 7. Piston 108 then abuts watertightness stopper 109, while piston 107 remains stationary since it is held by compressed air pressure from bore 114.

In a third operational sequence, when sterilization of the chamber is complete, the system passes to the "sampling" mode. The electric valve associated with bore 115 has three positions-compressed air intake, purge, closed-and after closure, compressed air is admitted through bore 118. When piston 104 advances it uncovers bore 112, which results in filling of the chamber of the stem of piston 104 (without evacuation) with the vapor/air mixture, and then uncovers bore 110 thus establishing a vapor circuit through bores 122, 112, 110, 111 which sterilizes the stem of piston 104 and the chamber in which it moves. According to the operational sequence 4 shown in FIG. 9, when piston 104 moves left and makes contact with the left shoulder of chamber C3, it is possible to stop the intake of vapor. The electric valve admitting vapor at opening 122 is then closed after the purge valve is closed at opening 111.

Figure 11A:
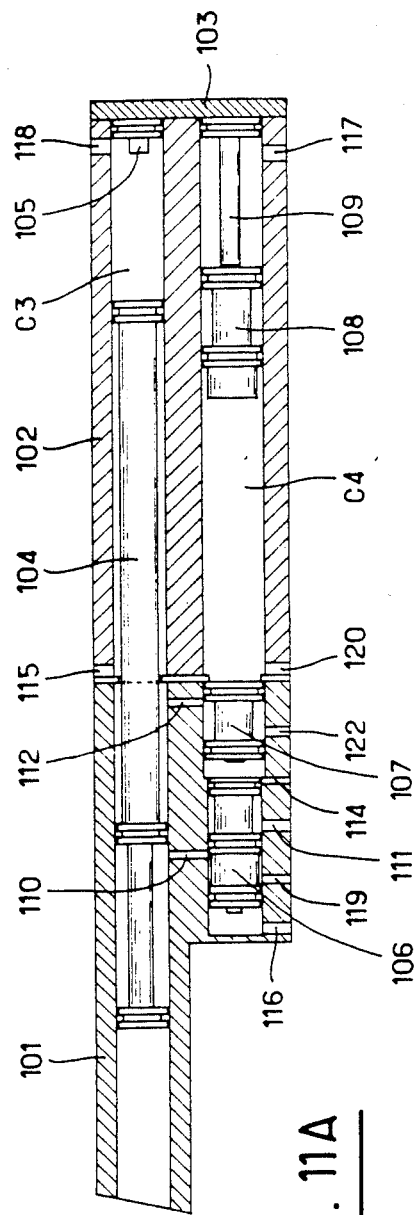
FIGS. 11A and 11B are, respectively, views analogous to FIG. 1, during dilution of sampled liquid.
Figure 11B:
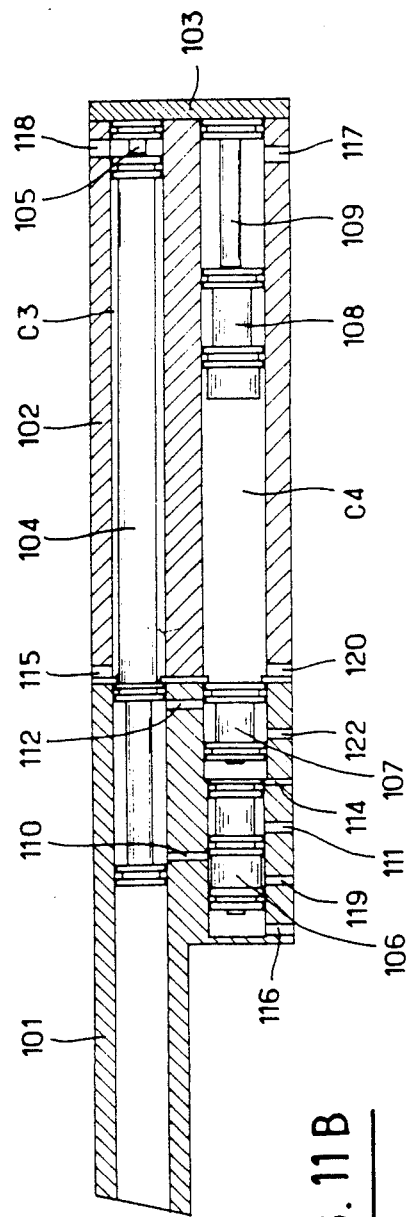

In the operational sequence shown in FIGS. 11A and 11B, bore 118 is under atmospheric pressure and compressed air is admitted through bore 115 producing withdrawal of piston 104 and pressurization of the chambers of pistons 106 and 107 respectively.

Piston 104 thus moves to the right. As soon as the sampling chamber opens into bore 110, this is detected by a sensor, not shown in the diagrams, which detects the position of piston 104. The command valve for opening 114 reaches atmospheric pressure and compressed air passes through opening 116, causing displacement of piston 106 to the right end-stop, as shown in particular in FIG. 11A. Bores 110 and 119 then communicate, pressure 119 being atmospheric. Piston 104 can then continue to move to the right until it abuts watertightness stopper 105, as shown in particular in FIG. 11B. Residual pressure in the annular space of piston 106 begins to force liquid along the trajectory of bores 112, 110, 119. It is convenient if piston 104 ceases to move at the moment when the sampling chamber communicates with opening 110, this pause being used to displace piston 106 in order to avoid complete abutment of piston 104 at stopper 105 to the right while piston 106 is still to the left and piston 107 to the right. Pressure imbalance between the respective annular spaces of pistons 106 and 107 could force sampling chamber liquid back through opening 112 towards bore 122.

Figure 12:
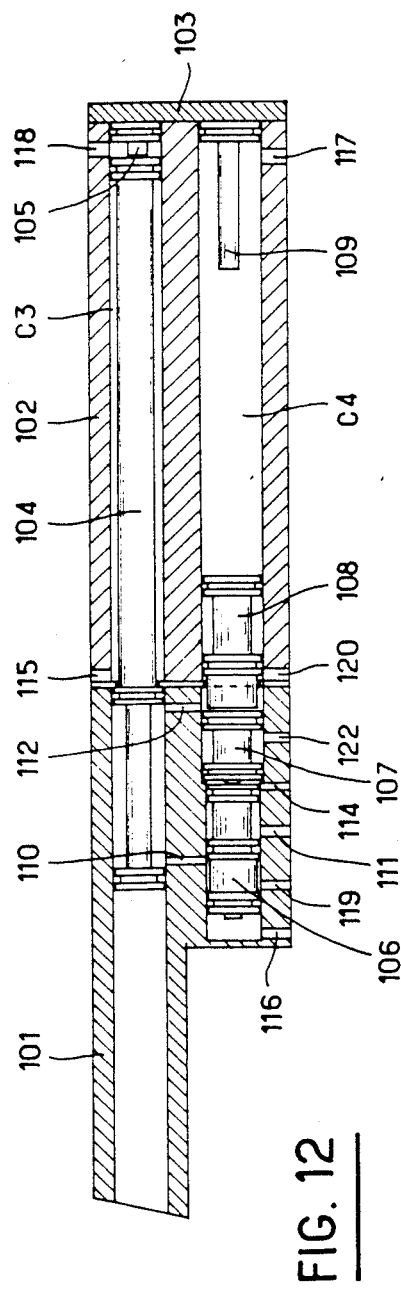
FIG. 12 is a view analogous to FIG. 1, at the end of dilution.

In the operational sequence shown in FIG. 12, compressed air passes through bore 117, while pressure is maintained in 116, causing, under the thrust of piston 108, forward motion of the liquid column which displaces piston 107 and uncovers bore 112, piston 107 abutting piston 106. Liquid passes into the sampling chamber, flows back through bore 110 and exits through bore 119. The end of piston 108 then fits into the shoulder zone of chamber C4.

Figure 13A:
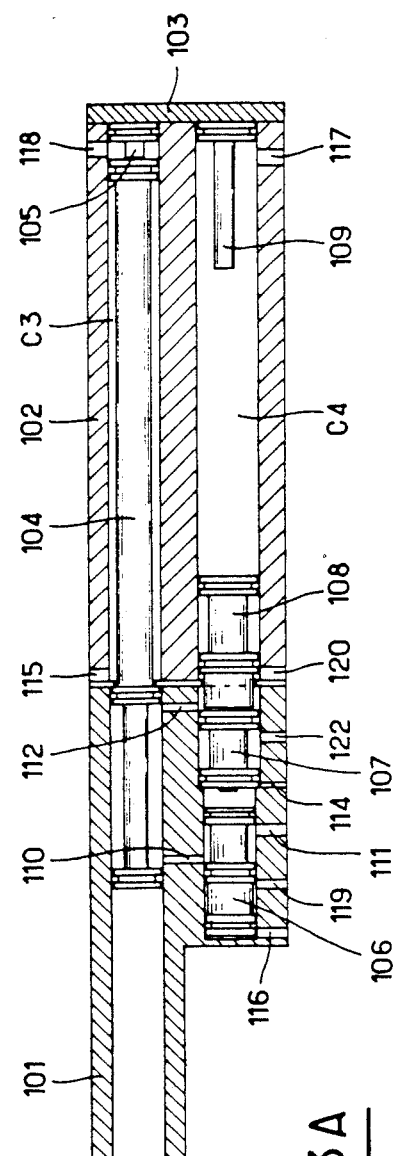
FIGS. 13A and 13B are, respectively, views analogous to FIG. 1, during resetting of components for a new sterilization cycle.
Figure 13:
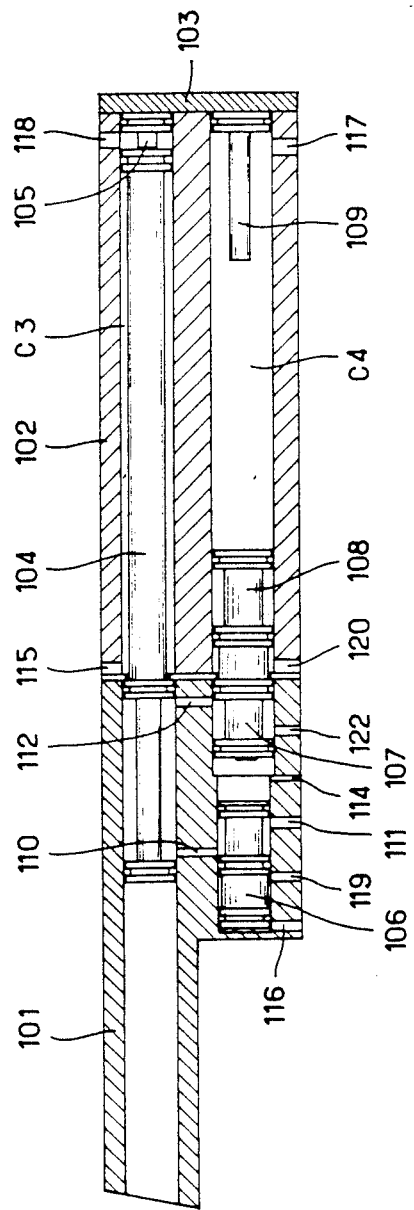

In the operational sequence shown in FIGS. 13A and 13B, it is possible to begin a new sterilization cycle, given that the dilution cycle is complete. For this purpose, bore 116 is brought to atmospheric pressure. Pressurization of bore 114 positions piston 106 for sterilization, the trajectory through bores 110 and 111 being opened up. Piston 107 is held by piston 108 as shown in particular in FIG. 13A. Bore 117 is then brought to atmospheric pressure. Piston 107 pushes back piston 108 and opens up the passage through vapor inlet bores 122 and 112. It is important that bore 119 then be closed before the passage through bores 122, 112 is opened, so as to eliminate the risk of introduction of vapor during sampling, the vapor then being admitted by the valve associated with bore 122, as shown in particular in FIG. 13B. The operator is then able to perform sequence 1.

The sampling device according to the present invention allows control of culture medium sterility while performing real operational cycles over several days. According to a preferred embodiment, it is possible, for example, to operate a 20-liter fermentation vessel under normal culture conditions, provided that handling likely to cause contamination and inoculation is avoided. After normal fermentation, the sampling device according to the invention can supply an analyzer, for example an apparatus using the principle of enzyme electrodes, in order to carry out rapid assays of organic molecules in liquid medium. The efficacy of any apparatus requiring samples of fixed volume improves markedly upon combination with the sampling device according to the present invention. Development of the present invention was only possible through active collaboration between the enzyme technology laboratory of the Universite Technologique de Compiègne, which is associated with the Centre National de la Recherche Scientifique N.338, and the inventors. According to the present invention, therefore, a solution is provided to the problem of automatic sterile sampling of culture medium, while obtaining fixed-volume samples to which various analytical methods can be applied.

The foregoing detailed description in reference to the appended figures has been given for clearness of understanding only, and no unnecessary limitations should be understood therefrom, as modifications will be obvious to those skilled in the art. Hence, the shape of the pistons may be altered, to make them telescopic or of variable geometry, while respecting the conditions of watertightness necessary within the chambers. Likewise, while pneumatic means have been used, any means of actuating the pistons may be used, provided that the conditions of watertightness and sterility needed for efficacious operation of the device according to the invention are respected.

What is claimed is:

1. A device for preserving sterility during the taking of a sample for analysis from culture medium containers, said device comprising a holder containing a first, sampling chamber which encloses a first sliding piston fitted at one end with means for obtaining a sample for analysis, and a second dilution chamber linked to the first chamber by a duct, said second chamber being divided into two parts by a bearing means against which abut at least second and third pistons which may slide respectively on opposite sides of the bearing means, said second chamber including at least one inlet for dilution solvent.

2. A device according to claim 1, wherein the first sliding piston is provided with a shoulder in a zone opposite the sample obtaining means.

3. A device according to claim 1, wherein between the first, second and third pistons and walls of corresponding chambers are fitted watertightness means.

4. A device according to claim 3 wherein said watertightness means are toric rings.

5. A device according to claim 1, wherein the sample obtaining means comprises a toric chamber fitted around the first sliding piston.

6. A device according to claim 1, wherein the dilution chamber is provided with a stop of a size chosen so as to determine a dilution volume, which is limited by opposite faces of the second and third pistons and internal faces of the dilution chamber.

7. A device according to claim 6, wherein the stop is movable and actuated by external means allowing adjustment of the dilution volume, and hence of a sample dilution factor.

8. A device according to claim 7, wherein the external means for actuating the stop consists of a computer-controlled stepping motor.

9. A device according to claim 1, wherein the first, second and third pistons are actuated by motor means selected from the group consisting of hydraulic, pneumatic and electromagnetic types.

10. A device according to claim 1, wherein when pneumatic means supplied from a source of compressed air are used to actuate the pistons, four means defining inlet-outlet openings are respectively provided in the chambers.

11. A device according to claim 1, wherein the dilution chamber includes an inlet for a sterile vapor/air mixture intended for purging and washing of the dilution chamber.

12. A device according to claim 1 in combination with motor means, an automatic cam device and inlet electrical valves, said motor means being controlled by said automatic cam device intended to control according to a preset cycle, said inlet electric valves ($V_1$, $V_2$, $V_3$, $V_4$, $V_5$, $V_6$, $V_7$) provided for admission of various liquids into the sampling device.

13. A device according to claim 12, wherein a desired cycle of valves is controlled by computer means.

14. A device according to claim 1, comprising two joined bodies and defining a first, upper, cylindrical, sampling chamber and a second lower, cylindrical, dilution chamber, the first chamber containing a piston shaped to define a peripheral sampling space while the second chamber contains three sliding pistons.

15. A device according to claim 14, wherein the bodies are both coupled at one of their ends to a plate forming a support for stoppers or watertightness stops fitted respectively in the chambers.

* * * * *